United States Patent [19]

Park et al.

[11] Patent Number: 5,330,768
[45] Date of Patent: Jul. 19, 1994

[54] CONTROLLED DRUG DELIVERY USING POLYMER/PLURONIC BLENDS

[75] Inventors: Tae G. Park, Cambridge, Mass.; Smadar Cohen, Petach-Tickva, Israel; Robert S. Langer, Newton, Mass.

[73] Assignee: Massachusetts Institute of Technology, Cambridge, Mass.

[21] Appl. No.: 726,349

[22] Filed: Jul. 5, 1991

[51] Int. Cl.$^5$ .............................................. A61K 9/16
[52] U.S. Cl. .................... 424/501; 424/426; 424/484; 424/486; 424/489; 424/600; 514/2; 514/23; 514/772.1; 514/964; 514/963
[58] Field of Search ............... 424/484, 486, 426, 489, 424/501; 514/963, 964, 772.1

[56] References Cited

U.S. PATENT DOCUMENTS

| | | | |
|---|---|---|---|
| 4,702,917 | 10/1987 | Schindler | 424/423 |
| 4,757,128 | 7/1988 | Domb et al. | 528/271 |
| 4,789,724 | 12/1988 | Domb et al. | 528/176 |
| 4,857,311 | 8/1989 | Domb et al. | 528/271 |
| 4,886,870 | 12/1989 | D'Amore et al. | 424/78 |
| 4,888,176 | 12/1989 | Langer et al. | 424/426 |
| 4,891,225 | 1/1990 | Langer et al. | 424/428 |
| 4,913,903 | 4/1990 | Sudmann et al. | 424/484 |
| 5,013,769 | 5/1991 | Murray et al. | 424/486 |
| 5,084,267 | 1/1992 | Damani | 424/426 |

OTHER PUBLICATIONS

Leong, et al., J. Med. Biomed, Mater. Res. 19, 941 (1985).
Leong, et al., J. Med. Biomed, Mater. Res. 20, 51 (1986).
Rosen, et al., Biomaterials 4, 131 (1983)
Kern, et al., Journal of Polymer Science XV, 183–192 (1955).
Gesner, et al., Polybends 10, 794.
Dobry, et al., Journal of Polymer Science 2, 90, (1947).
Paul, et al., Polymer Blends Edited by D. R. Paul et al. 1, 1 (1978).
Pitt, et al., Proceed. Intern. Symp. Control. Rel. Bioact. Mater., 14, 75, (1987).

Primary Examiner—Thurman K. Page
Assistant Examiner—James Spear
Attorney, Agent, or Firm—Kilpatrick & Cody

[57] ABSTRACT

A new series of degradable polymeric matrices were prepared by blending polymers that degrade by hydrolysis such as poly(L-lactic acid)(PLA), and nonionic Pluronic ™ surfactants, block copolymers of polyethyleneoxide (PEO) and polypropyleneoxide (PPO). The water content of the polymer blend films was controlled by mixing different types of block copolymers and by adjusting their amount. In aqueous solution, the blends revealed the typical liquid-crystalline phase transition of Pluronic ™ polymers, suggesting the formation of a gel-like structure within the polymer skeleton. Poly(lactic acid) degradation rates were not affected by the blending procedure, although the hydration degree in these matrices was higher. When used as drug-releasing matrices, these blends extended protein release and minimized the initial protein burst, as compared to the pure polymer.

3 Claims, 3 Drawing Sheets

CONTROLLED DRUG DELIVERY USING POLYMER/PLURONIC BLENDS

BACKGROUND OF THE INVENTION

The United States government has rights in this invention by virtue of grants from the National Science Foundation.

This is generally in the area of polymeric controlled drug delivery devices, and specifically in the area of polymer/Pluronic TM blends for controlled delivery.

Recently, a variety of biodegradable polymers have been widely used as implantable biomaterials, such as prosthetics and tissue support matrices, and as drug delivery devices. The main advantage of using the biodegradable polymer is that no retrieval of the device is needed after a particular usage. The degradation time of the polymer as well as the release properties of a particular drug from the polymer can also be varied, for example, from months to years and from linear to staggered release, by varying molecular weight and chemical composition of the polymer. The chemical composition is varied by selection of the monomers and copolymerization with other biodegradable monomers. The ratios of amorphous to crystalline and hydrophilic to hydrophobic properties are largely responsible for determining the degradation time.

Although widely used and approved for use in vivo by the United States Food and Drug Administration, it is difficult to obtain the desired release profile using many of these biocompatible, biodegradable polymers such as poly(lactic acid) (PLA). PLA is widely used since the degradation product, lactic acid, is metabolized in the body. There have been several studies on protein delivery using PLA as a matrix, in which a significant portion of the loaded protein was often released at the initial stage as a single burst, rather than over an extended period of time, regardless of the rate of degradation of the matrix.

Two methods have been utilized to improve the release profile of compounds from these polymers: copolymerization of the lactic acid with glycolic acid to form poly(lactide-glycolide) copolymers and mixing the compound encapsulated in PLA with the same compound encapsulated in other polymers or copolymers. However, neither method has been totally successful in achieving the desired release rate, or has proven to be difficult to control during manufacture and administration.

Due to processing considerations, the mechanical properties of the polymer are important. The polymer must be sufficiently hard but flexible to allow incorporation of drug, must be soluble in solvents not denaturing the protein to be encapsulated, or melt at a low enough temperature to allow incorporation of the drug without denaturation of the drug. These are particularly a problem with many of the heat labile drugs.

Polymer blends, a physical mixture of two different polymers, exhibit advantageous physical and mechanical properties that each individual polymer does not have. Depending on thermodynamic compatibilities of the two chosen polymers, different degrees of phase separated blends can be obtained. However, only a few applications of polymer blending technology for drug delivery matrices have been attempted, as reported by Younes and Cohn, *European Polymer J.* 11, 765 (1988). For example, PLA has been blended with degradable and nondegradable polymers such as poly(D-lactic acid), as reported by Loomis, et al., *ACS Polymer Preprint* 32, 55 (1990), poly(glycolic acid), as reported by Cha and Pitt, *Biomaterials* 11, 108–111 (1990), and poly(ethylene-vinyl acetate), as reported by Dollinger and Swan, *ACS Polymer Preprint* 32, 429 (1990), in an effort to modify PLA morphology and its degradation profile.

It is therefore an object of the present invention to provide biodegradable polymeric compositions for controlled drug delivery, and methods for making and using the compositions, wherein the compositions have desired mechanical and release properties as compared with PLA polymeric compositions for controlled drug delivery.

SUMMARY OF THE INVENTION

Biodegradable, biocompatible matrices for drug delivery, including films and microspheres, are formed by blending polymers degrading by hydrolysis such as poly(lactic acid) and Pluronic TM surfactants (block copolymers of polyethyleneoxide (PEO) and polypropyleneoxide (PPO)). Physico-chemical and morphological properties such as phase separation behaviors, degradation rates and surface properties of PLA/Pluronic TM blend films have been characterized by differential scanning calorimetry (DSC), infrared spectroscopy (IR), gel permeation chromatography (GPC) and scanning electron microscopy (SEM). (PEO/PPO/PEO) block copolymers exhibit a wide range of hydrophilicity/hydrophobicity as a function of PEO/PPO ratio, so that one can adjust the degree of phase separation with the polymer. Water content of the polymer can be controlled by blending different kinds of block copolymers and by adjusting the relative ratios. Other polymers that can be blended with the Pluronics TM include polyanhydrides, polyorthoesters, and poly(amino acids).

Compounds to be delivered are incorporated into the polymeric composition by mechanical mixing, or by solvent or melt casting. The blends are biocompatible, biodegradable, and exhibit desirable release profiles of the incorporated compounds, as demonstrated using PLA/Pluronic TM blends containing bovine serum albumin.

DETAILED DESCRIPTION OF THE INVENTION

Figure 1A:
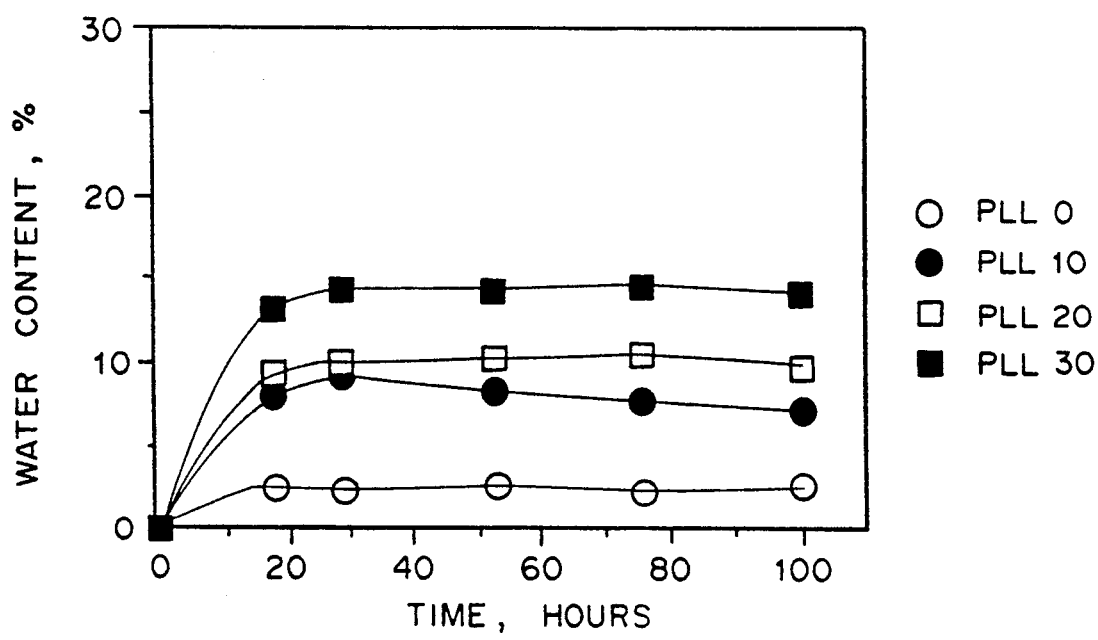
FIG. 1 are graphs of the percent water content of PLA/L-101 (FIG. 1A) and PLA/F-108 (FIG. 1B) blend films without bovine serum albumin (BSA) loading incubated in pH 7.4 and at 37° C. PLL(F) X indicates PLA/L-101 (F-108) with X weight fraction of L-101 (F-108) in the blend.

Biodegradable, biocompatible matrices for drug delivery, including films and microspheres, are formed by blending polymers degrading by hydrolysis such as poly(lactic acid) and Pluronic TM surfactants (block copolymers of polyethyleneoxide (PEO) and polypropyleneoxide (PPO)). (PEO/PPO/PEO) block copolymers exhibit a wide range of hydrophilicity/hydrophobicity as a function of PEO/PPO ratio, so that one can adjust the degree of phase separation with PLA. Water content of the polymer can be controlled by blending different kinds of block copolymers and by adjusting the relative ratios.

Physico-chemical and morphological properties of polymer/Pluronic TM blends can be characterized by differential scanning calorimetry (DSC), infrared spectroscopy (IR), gel permeation chromatography (GPC) and scanning electron microscopy (SEM). DSC studies of PLA/Pluronic TM blend films suggest that some degree of Pluronic TM miscibility in the amorphous region of PLA can be obtained by selecting polymer surfactants with suitable hydrophobicities, which results in formation of films with an overall intact surface morphology (SEM). In aqueous solution, the blends revealed the typical liquid-crystalline phase transition of Pluronic TM polymers, suggesting the formation of a gel-like structure within the PLA skeleton. PLA degradation rates were not affected by the blending procedure although the hydration degree in these matrices was higher, suggesting a complex mechanism of hydrogen bond formation between the carboxylic groups of PLA and the ethers of the surfactant polymers. When used as drug-releasing matrices, these blends extended protein release and minimized the initial protein burst, compared to the pure polymer.

Polymers degrading by hydrolysis:

Polymers that can be blended with the Pluronics TM include poly(lactic acid), poly(glycolic acid), polyorthoesters, polyanhydrides, and poly(amino acids). The polymers are biocompatible and biodegradable, being susceptible to hydrolysis. The polymers can be blended with the Pluronics TM alone, or in combination with other polymers. The polymers are all well known in the drug industry, many approved by the U.S. Food and Drug Administration for administration to patients, and either available commercially or synthesizable using published methodology.

Pluronics TM:

Nonionic Pluronic TM surfactants, polyethyleneoxide (PEO)/polypropyleneoxide (PPO)/polyethyleneoxide (PEO) block (ABA type), (PEO/PPO/PEO) block copolymers, exhibit a wide range of hydrophilicity/hydrophobicity as a function of the PEO/PPO ratio, so that one can expect to obtain different phase separated morphologies with polymers such as PLA as well as different degrees of hydration of the matrix. In particular, hydration plays an important role in determining polymer degradation via hydrolysis of the ester backbone. These polymeric surfactants exhibited minimal toxicities in vivo and some of them are in clinical use, as described by BASF Corporation in their 1989 *Technical Bulletin;* Attwood, et al., *Int. J. Pharm.* 26,25 (1985); and U.S. Pat. No. 4,188,373 to Krezanoski.

These materials can be obtained from BASF Corporation.

Methods for blending Polymers and Pluronics TM:

The polymer and Pluronic TM are blended in a ratio of between approximately 10:90 and 90:10. For drug delivery purposes, a preferred ratio is in the range of between 80:20 and 60:40, polymer to Pluronic TM.

The blends can be prepared by mixing polymer and Pluronic TM in solution prepared by dissolution in an appropriate solvent or by melt mixing, using standard techniques known to those skilled in the art. Examples of suitable solvents include hexane, methylene chloride, chloroform, and other organic solvents in which both the polymer and block copolymers are soluble. In general, solvent preparation is used to prepare porous matrices and melt mixing is used to prepare relatively non-porous matrices. Selection of the appropriate method is also dependent on the material to be incorporated. For example, for delivery of a temperature labile protein from a PLA/block copolymer blend, the protein would be incorporated using the solvent preparation, since PLA has a melting temperature of 170° C. On the other hand, polyanhydrides have melting temperatures that are lower, for example, 80° C., so the melt mixing technique might be useful in this case.

Compositions to be incorporated into the polymeric compositions:

In the preferred embodiment, biologically active compounds are incorporated into the polymer blends. These include inorganic compounds, proteins (including peptides), carbohydrates, and other types of organic molecules such as steroids. Non-biological materials such as pesticides, herbicides, and fertilizers can also be incorporated.

The polymeric composition is designed to meet the required biocompatibility needs (low, in the case of herbicides, high, in the case of controlled drug delivery) and degradation rate, ranging from weeks to many months.

The present invention will be further understood by reference to the following examples.

Example 1: Preparation of PLA/PEO-PPO-PEO blend films

A series of PLA/PEO-PPO-PEO blend films were prepared by a solvent casting method. Physical and morphological studies of the resultant films were carried out using differential scanning calorimetry (DSC), infrared spectroscopy (IR), scanning electron microscopy (SEM), and gel permeation chromatography (GPC). A model protein drug, bovine serum albumin, was loaded into the polymer blend films to examine the effect of morphological changes in polymer blends on protein release patterns (i.e., extent of initial protein burst and release period).

PLA (MW 100,000) was obtained from Polysciences. GPC analysis revealed a weight average and number average molecular weight of 71,000 and of 60,000, respectively. Three (PEO/PPO/PEO) block copolymers were physically blended with the PLA. Pluronics TM, (PEO/PPO/PEO) block copolymers, F-108, L-101, and P-104, were obtained from BASF Performance Chemicals, Parsippany, N.J. These copolymers are also known as Poloxamers, especially in Europe and Japan. All other reagents were analytical grade.

For blend film preparation, PLA was dissolved in 3 ml of methylene chloride with varying amounts of Pluronic TM (BASF Corp.). The amount of polymer mixture was 0.5 g. The polymer solution was cast onto a pre-silanized glass petri-dish and the solvent was evaporated at room temperature overnight and under vacuum.

For protein loaded blend films, 20 mg of fluorescein isothiocyanate labelled bovine serum albumin (FITC-BSA) (Sigma Chemical Co.) dissolved in 0.5 ml of 0.1 M phosphate buffer pH 7.4 was emulsified in the polymer solution with sonication and/or subsequent vortex mixing, and then cast onto the glass plate.

PLA, poly(lactic acid-glycolic acid) (PLGA) and PLA/Pluronic TM microspheres were prepared according to S. Cohen, et al., *Pharm. Res.* (in press 1991), as follows using a modified solvent evaporation method using a double emulsion. Briefly, 10 mg protein was dissolved in 50 μl double-distilled water and poured into 1 g polymer dissolved in 1 ml methylene chloride. The mixture was mixed for 1 min. using a vortex mixer at maximum speed (Vortex Genie, Scientific Inc.) or probe sonicated (Model VC-250, Sonic & Materials Inc.) at output 4 (50 W), for 30 sec. to form the first inner emulsion ($W_1/O$). The emulsion was poured, under vigorous mixing using a magnetic bar, into 2 to 5 ml of aqueous 0.1% to 1% polyvinyl alcohol (PVA) saturated with methylene chloride to form the second emulsion [$(W_1/O)W_2$]. The resulting double emulsion was poured into 200 ml 0.1% to 0.3% PVA and continuously stirred for 3 hr at room temperature until most of the methylene chloride evaporated, leaving solid microspheres. The microspheres were collected by centrifugation (Sorvall DoPont Model RC-5B, 1000 g for 10 min.), sized using sieves with apertures of 100 μm, and freeze-dried (16 hr, Freeze Dryer, lab Conc) into a powder.

The following methods were used to analyze the resulting materials.

Water Content Determination

Dry blend films without BSA loading were incubated in phosphate buffered saline (PBS) pH 7.4 at 37° C. At preset time intervals, hydrated samples were taken and weighed after blotting the surface water with tissue. Weight change of the blend films was based on the difference of dry weights before and after 1 week incubation at 37° C. in the buffer. The wet weight included the amount of free water in the pore region of the matrix, the amount of bound water associated with the polymer, and the dry weight of the polymer. Dry weights were determined after complete drying of the hydrated samples under vacuum for over 24 hr. Water contents were then calculated based on the difference in dry and wet weights.

Infrared (IR) Spectroscopy

IR (Perkin Elmer Model 1420) spectra were taken by dissolving the blend films in methylene chloride and casting them onto sodium chloride cells.

Differential Scanning Calorimetry (DSC)

DSC (Perkin Elmer 7 Series) thermograms were taken using a standard aluminum pan. Nitrogen was used as a sweeping gas and the heating rate was 10° C./min. 3–5 mg samples were loaded without further heat treatment. For hydrated samples, volatile sample sealer was used to prevent water evaporation during heating. All the samples for DSC were dehydrated or hydrated blend films without BSA loading.

Scanning Electron Microscopy (SEM)

Samples were coated with gold particles to a thickness of 200–500 A. Surface morphology of PLA/Pluronic TM blend films was examined using an Amary 1000 A scanning electron microscope at 20 kv electron beam radiation.

Gel Permeation Chromatography (GPC)

The molecular weight of PLA was determined by a Perkin Elmer Series 10 Liquid Chromatograph with a LC-25 RI detector and using a Phenomenex PL gel 5μ Mixed column. Chloroform was used as an eluant. Chromatograms were processed by GPC 5 software to calculate the weight average molecular weight of the polymer using polystyrene as a standard.

Protein Release Study

Protein (FITC-BSA) loaded polymer blend films were punctured in the shape of discs (6.35mm in diameter and about 0.5mam in thickness) and incubated in 5 ml of PBS, pH 7.4, at 37° C. to characterize the release rates. The amount of released FITC-BSA at various time intervals was assayed by monitoring the absorbance at 495 nm of the PBS.

The amount of protein in the microspheres was determined by two methods: directly by recovering the protein from the microspheres and indirectly by measuring the residual unentrapped protein in the outer water phase. Three methods for protein extraction can be used: (1) microspheres are dissolved in 3 ml methylene chloride and the protein extracted into 4 ml distilled water: (2) microspheres are dissolved in 2 ml 90% acetonitrile aqueous solution and protein extracted into 8 ml 0.1 M phosphate buffer, pH 7.4; and (3) microspheres are suspended in distilled water and bath-sonicated for 15 min. The aqueous solution is filtered through a 0.45 μm filter (Acro LC25, Gelman Sciences Inc.) and the amount of protein determined by absorbance at 495 nm (Fast Scan 553, Perkin Elmer).

Water Contents in Polymer Blends

Pluronic TM surfactants exhibit a wide range of different hydrophilic/hydrophobic properties depending on the molar ratio of the hydrophilic ethylene oxide (EO) unit and the hydrophobic propylene oxide (PO) unit in their block copolymers. Table 1 lists the physicochemical properties of the three Pluronic TM surfactants examined, F-108, P-104, and L-101. L-101 which has a low ratio of EO to PO is the most hydrophobic (i.e., least water soluble).

TABLE 1

| Physical characteristics of Pluronics TM | | | |
|---|---|---|---|
| Pluronic TM | F-108 | P-104 | L-101 |
| Physical State at room temperature | solid | paste | liquid |
| Water solubility | soluble | moderate | insoluble |
| Molecular weight | 14,600 | 5,900 | 3,800 |
| Ethylene oxide weight % | 80 | 40 | 10 |

Since these block copolymers have an amphiphilic structure, normally found in surfactants, they exhibit temperature dependent theological properties in aqueous solutions, that is, gelation above a certain temperature, as reported by Wanka, et al., *Colloid & Polymer*

Sci., 268, 101-117 (1990). The gel formation is particularly pronounced in water soluble Pluronic TM surfactants which have high EO/PO ratios. Water-Pluronic TM interactions may play an important role in such a thermal phase transition of aqueous polymer solutions.

Example 2: Alteration of the Physical Properties and Rate of Degradation by Hydrolysis of PLA/Pluronics TM blends A typical biodegradable PLA is relatively hydrophobic and has a semi-crystalline structure. Degradation proceeds via nonenzymatic, hydrolytic breakage of the ester backbone bond. Water accessibility to these bonds determines the rate of degradation. It takes months to years for complete degradation of PLA matrices, depending on the molecular weights, as reviewed by Holland, et al., *J. Controlled Release* 4, 155-180 (1986). Blending PLA with Pluronic TM produces different degrees of matrix hydration depending on the selection and amount of Pluronic TM blended with the PLA. Degradation is accelerated by a high water concentration in the vicinity of the hydrolytically-labile ester bond, as demonstrated using a variety of blend films, PLA/L-101, PLA/F-108, and PLA/P-104 (denoted as PLL, PLF and PLP).

The PLA/L-101 blend films are mechanically strong enough to handle, while the PLA/F-108 blend films are brittle with increasing F-108 amount.

Figure 1B:
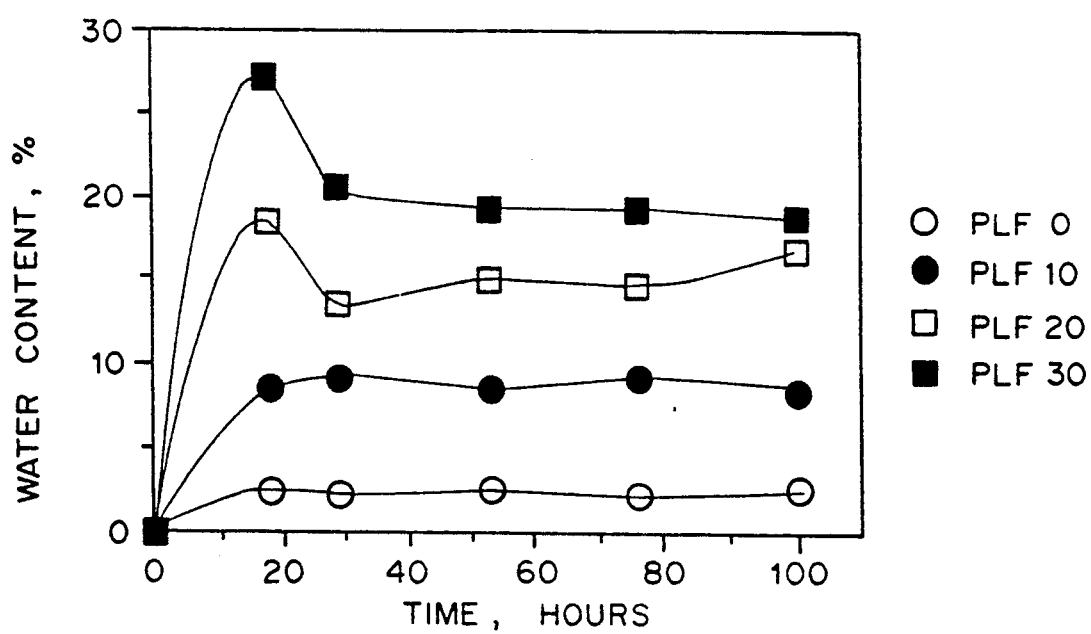

FIG. 1 shows the hydration degree for blends of PLA with L-101 and F-108 without BSA loading as a function of incubation time in PBS, pH 7.4, at 37° C. All blends showed high water content relative to the homogeneous PLA; the water content increased with increasing amounts of Pluronic TM in the blends. The more hydrophilic F-108 blends exhibited higher water contents than the L-101 blends. These blends showed an initial overshoot followed by a decrease in the water content. It is believed that this is due to a rapid diffusion of the highly water soluble F-108 out of the blend, as water penetrates and dissolves it. This is supported by the weight change measurements of the PLA/P-108 (70/30) blend that showed a net dry weight loss of more than 20% after one week incubation in PBS. Initially, it was thought that the PLA/F-108 blends might exhibit a small dry weight loss due to a gelation phenomenon at 37° C, caused by temperature-dependent water F-108 interactions in the pore of the blend matrix. The weight loss study was separately carried out after one week incubation, since leaching of F-108 (M.W. 14,600) out of the blend matrix could have been a complex mixture of processes such as water diffusion-in, F-108 dissolution, and F-108 diffusion-out. However, the results showed that F-108 leaches out of the polymer blend film upon hydration, presumably leaving water-filled pores, which might be used to create highly porous biodegradable matrices to be manipulated as a scaffold for certain applications such as cell delivery. The porosity of the polymer matrix can be controlled by adjusting the amount of incorporated Pluronic TM.

Figure 2:
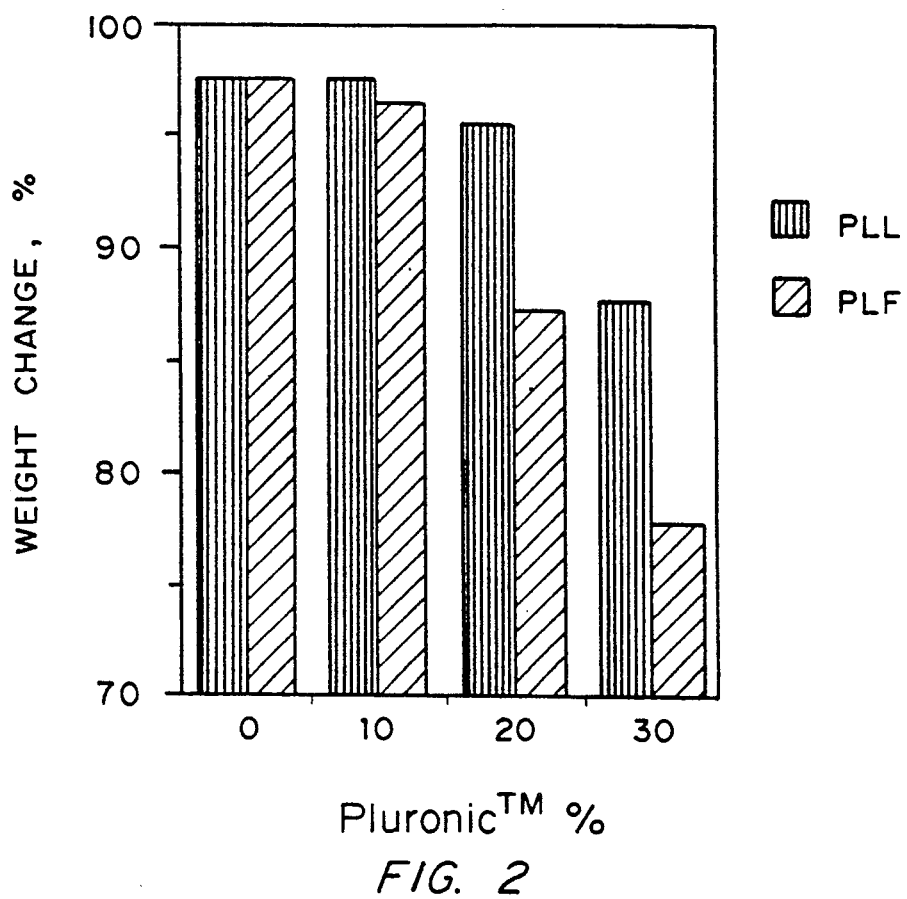
FIG. 2 is a graph of the percent remaining weight of PLA/L-101 (PLL) and PLA/F-108 (PLF) blends without BSA loading after one week incubation in buffer, as a function of the percent Pluronic TM.

A relatively high amount of the hydrophobic L-101 was still retained in the blend matrices after this time period, as shown in FIG. 2. In the case of PLA/P-104 (80/20) blend, the % weight decrease after 1 week was 7.5%, an intermediate value between L-101 (4.5%) and F-108 (2.6%) blends having the same initial ratios of Pluronic TM (20%), showing that the water solubility of Pluronic TM is indeed an important parameter in determining the amount of Pluronic TM leaching out of the blend matrices. The presence of the L-101 in the blend films was further confirmed by IR spectra acquired after a 30 day incubation. A broad band at 2870 $cm^{-1}$, corresponding to the $-CH_2-$ stretching on the PO unit of L-101, appeared and its size increased with the increasing amount of L-101 in the blend. The peaks at 2980 and 2930 $cm^{-1}$ are assigned to $-CH$ anti-symmetric stretching and $-CH_3$ stretching band of PLA.

Phase Behavior in Polymer Blends

The thermodynamic compatibility between PLA and Pluronic TM is expected to vary depending on the type of Pluronic TM. Although the water solubility of Pluronic TM changes with the ratio of PEO/PPO, the solubility parameters of hydrophobic PPO segment (7.5 -9.9), reported by Olabisi, et al., Chapter 3 in *Polymer-polymer Miscibility* (Academic Press, NY 1979), and PLA (9.5-9.8), reported by Cohen and Younes, *J. Biomed. Mater. Res.* 22, 993-1009 (1988), are close so some degree of phase mixing can be expected. Nevertheless, since no significant acid-base interaction and/or hydrogen bonding between PLA and Pluronic TM can be expected except for those between the hydroxyl and carboxyl end groups in PLA, and the backbone ether and terminal hydroxyl group in Pluronic TM, PLA/Pluronic TM blends might have a phase separated domain structure, especially since the PLA/Pluronic TM blend films are all opaque, indicating the phase separated structure, while the homo-PLA film is translucent. However, the physical appearance of the blend film is only indirectly indicative of polymer miscibility, and the degree of phase separation can not be assessed quantitatively. Thus, DSC studies were carried out to examine and quantify the extent of phase separation. A shift in glass transition temperature (Tg) provides direct evidence of polymer miscibility, as reported by Olabisi, et al., (1979), the teachings of which are incorporated herein. While PLA has a clear Tg around 55.9° C., the PLA/Pluronic TM blends exhibited a rather broad endotherm around the glass transition temperature of PLA, making it hard to determine the precise Tg as a function of Pluronic TM weight fraction. Nevertheless, the estimated Tg's for the blends were lower than that of PLA, as shown in Table 2, suggesting the disturbed amorphous region of PLA by the Pluronic TM which may act as a plasticizer.

The crystalline melting temperature ($T_m$) of PLA is another method used to evaluate the extent of phase separation in the blend. When two polymers are compatible in the amorphous state, the $T_m$ is depressed as a result of the disturbed order in the crystalline phase. As shown in Table 2, a slight shift in $T_m$ of PLA was observed upon blending more hydrophobic Pluronic TM surfactant with the PLA, while $T_m$ is essentially the same when blending with F-108 and P-104. These results indicate a phase separation in the cases of F-108 and P-104 blends, and a slight phase mixing in the hydrophobic L-101/PLA blend. The crystalline melting enthalpy (H) data shows the higher crystallinity values in blends of F-108 and P-104 than in L-101 blend or PLA. Since $T_m$ is related to crystalline structure and size and delta H to crystallinity, this result implies that it is the crystallinity of PLA which is affected by blending with the hydrophilicity/ hydrophobicity of Pluronic TM while the crystalline structure of PLA is not disturbed very much.

The hydrophilicity/hydrophobicity of Pluronic TM appears to affect the nucleation and growth crystalline spherulites by changing the interfacial free energy between the crystalline and amorphous phase in the PLA. The hydrophobic L-101/PLA blend has a much smaller crystalline size than the F-108/PLA blend. There is also the phase mixing possibility between the amorphous regions of PLA and Pluronic TM surfactants because these regions have more polymer chain flexibility than the crystalline region for polymer-polymer miscibility. H decreases with the increase in Pluronic TM amount due to the smaller weight fraction of PLA in the blends. Although the calculated crystallinities (normalized to PLA fraction in the blend) are higher for the F-108 than that for the L-101 (Table 2), the decrease in delta H in the blends is more pronounced for the L-101 than the F-108 with increasing amount of Pluronic TM surfactants. This indicates that the hydrophobic L-101 may be more readily intermixed with the polymer chains of PLA in the amorphous region and is consistent with the finding that a smaller amount of L-101 is leached out during the incubation in buffer (see FIG. 2). Due to the leaching of the hydrophilic F-108 from the blend, only PLA/L-101 blends were further investigated for protein delivery applications.

TABLE 2

Effect of Pluronic TM blending on PLA crystalline melting enthalpy. Weight fraction of Pluronic TM is 20% in the blend.

| PLA/Pluronic TM Blends | $T_m$, °C. | H, J/g PLA | $T_g$, °C. |
|---|---|---|---|
| PLA (M.W 71,000) | 177.3 | 46.8 | 55.9 |
| PLA/F-108 | 177.3 | 50.7 | 47.9 |
| PLA/P-104 | 177.1 | 49.4 | N/A |
| PLA/L-101 | 176.5 | 46.1 | 52.9 |

Since blend films will be incubated in aqueous solutions, both in testing and in subsequent in vivo use, phase separation between PLA and the Pluronic TM L-101 should be considered in the presence of a third component, water. It is expected that water will preferably interact with the hydrophilic ethylene oxide part of a Pluronic TM surfactant that is entangled in the amorphous region of PLA. (PEO/PPO/PEO) block copolymers exhibit a complicated self-aggregation behavior in aqueous solution due to micelle formation. It has been reported that water-nonionic polymeric surfactant interactions lead to a liquid crystalline phase at low water concentrations. Thus, it is conceivable that in aqueous solution, an L-101-water liquid crystalline phase will be formed within the porous region of PLA.

The term "liquid crystalline" as used herein refers to any self-assembled and ordered molecular structure which includes the "gel" formation, often found in hydrophilic Pluronic TM surfactant-water system above a certain temperature range. DSC studies were carried out to prove the existence of such a liquid crystalline phase. A DSC thermogram of PLA/L-101 blend films, dried after 7 days incubation, did not show any noticeable peaks except for a very broad Tg around 60° C. and a crystalline melting peak of PLA around 175° C. In contrast, the hydrated films showed an apparent liquid crystalline phase transition peak which appears to shift to higher temperatures with an increasing amount of L-101 in the blend. It is suggested that a more ordered liquid crystalline phase may be formed as more L-101 is incorporated. The very broad endotherm for the PLA sample, apparently a typical Tg, may be due to the disturbed glassy structure by the hydration.

The surface compactness of the PLA/L-101 blends was examined by SEM. The homo PLA film surface has spherulites, crystalline domains along with pores which are probably formed by the rapid evaporation of the organic solvent. On the other hand, the surface of PLA/L-101 (80/20) film has a rough morphology without pores. The spherulite sizes are smaller than those observed with the PLA film, supporting the DSC data of a slight $T_m$ shift for the PLA/L-101 blends. A magnified view of the surface revealed that the PLA crystalline domains (spherulites) are covered by L-101 which appears to be also crystallized radially, suggesting the formation of ordered liquid crystalline phase in the hydrated state. Although L-101 is a liquid at room temperature, it is possible that PEO segments are crystallized while PPO segments are anchored on the spherulites. The SEMs also indicate that a rapid crystallization of PLA upon solvent removal induces spherulite formation, while the polymeric L-101 may be entangled within the amorphous PLA chains, producing an overall nonporous surface. The same surface morphology was observed after 1 week of hydration, again implying that no significant loss of L-101 from blend has occurred with time.

Degradation Studies

PLA has been known to degrade slowly because of its hydrophobic and semi-crystalline structure which does not allow fast water penetration. The degradation rate is proportional to water and ester concentrations, and is autocatalyzed by the generated carboxylic end groups. It can be expressed as follows:

Degradation rate = k[H$_2$O][COOH][Ester]

When Pluronic TM L-101 is blended with PLA, it is expected that the PLA degradation rate will be modified due to changes in water concentration. A more hydrated sample will be hydrolyzed faster due to water accessibility in the vicinity of the ester bonds.

Figure 3:
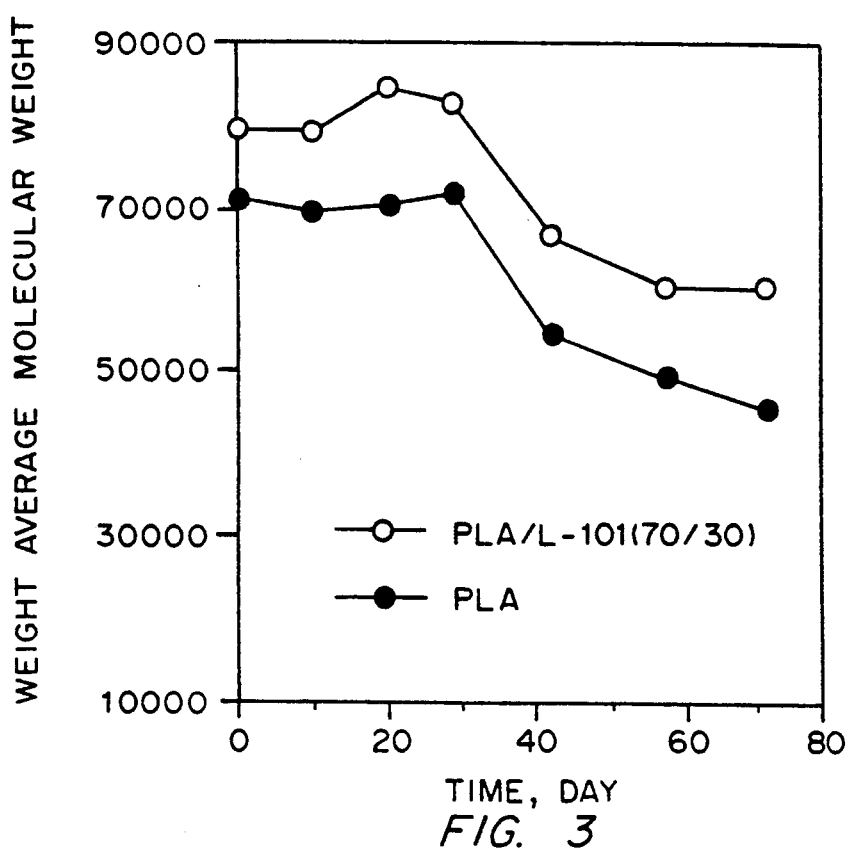
FIG. 3 is a graph of the weight average molecular weight degradation profiles for PLA and PLA/L-101 (70/30) blend films without BSA loading as a function of time (days).

FIG. 3 shows that the change in the molecular weights of PLA and PLA/L-101 (70/30) blend are approximately 10,000 higher than those of the homo PLA at all time points. This might be due to nonspecific chain entanglement and/or complex formation between PLA and L-101 polymer chain (MW 3,800) in chloroform via hydrogen bonding between the terminal carboxylic groups and the ether bonds of L-101. In fact, it is known that the polymers containing carboxylic acid groups are readily miscible with polyethers via hydrogen bonding. After an induction period of 30 days, both the PLA and the PLA/L-101 blend apparently start to degrade at a similar rate. The time lag observed in the degradation may be due to the slow hydration rate in the PLA crystalline region. Weight loss measurements revealed that the films retained their mass during the degradation period. This is consistent with the fact that random hydrolytic chain cleavage of the polymer backbone proceeds until a critical molecular weight is reached, from which weight loss begins with the diffusion of cleaved water soluble fragments out of matrix. The apparent similarity of the degradation rates for both samples suggests that L-101 does not significantly affect the overall degradation of PLA. This might be explained by the two opposite effects that are imposed by L-101 blending on PLA degradation. On one hand, L-101 increases matrix hydration, thereby enhancing the degradation rate. On the other hand, formation of hydrogen bonds between the terminal carboxylic groups of PLA and ether bonds of L-101 reduces the autocatalytic contribution of free carboxylic acid, thus decreasing the rate of degradation. Although the increasing hydration cleaves the ester linkage, the generated terminal carboxylic groups are not available for further catalytic degradation because of immediate hydrogen bonding with ether bonds.

Example 3 Protein Release from Polymer Blends

Protein release from polymeric matrices have been extensively studied in the past years, where variable release profiles were achieved by selecting suitable polymer matrices, shape, preparation method, protein loading, and particle size, and may other factors, as reviewed by Langer, et al., *Methods in Enzymology* 112, 399-422 (1985) and Cohen, et al., *Pharm. Res.* 8, 713-720 (1991). When matrices are prepared by solvent casting, the evaporation rate of the organic solvent plays an important role in the formation of pores in the matrix, eventually leading to protein dumping at an initial stage, i.e., the "burst" effect. Slow removal of the organic solvent at low temperatures is one way to decrease the burst effect.

Figure 4:
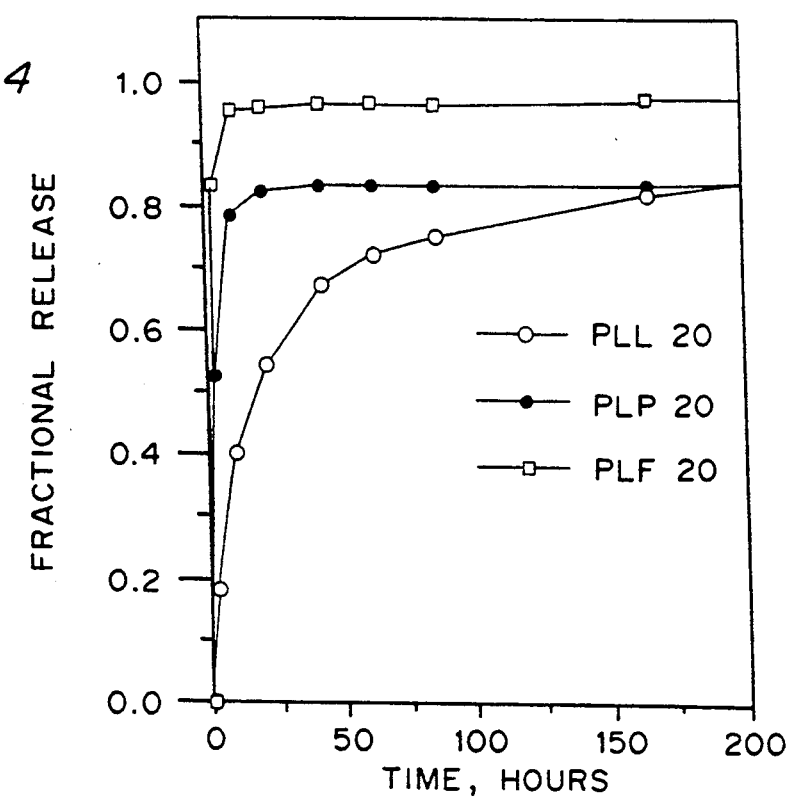
FIG. 4 is a graph of the fractional release over time (hours), demonstrating the effect of Pluronic TM blending on BSA release. Weight fractions of Pluronic TM are 20%.

The possibility of decreasing the protein burst was examined by blending PLA with Pluronisc TM, based on studies showing that blends of PLA and L-101 produced films with an intact surface morphology. FIG. 4 shows the effect of different Pluronic TM 0 blends on BSA release. The relatively hydrophobic Pluronic TM, L-101, was more effective than the hydrophilic F-108 in decreasing the initial protein burst as well as prolonging the release period. These results agree with the finding that the relatively hydrophilic Pluronic TM F-108 is quickly leached out, at the initial stage of incubation, leading to a fast BSA release, while the PLA/L-101 blend film, where L-101 is entangled with the amorphous PLA chains, delayed BSA release. The PLA/P-104 blend which has a moderate hydrophilicity/hydrophobicity exhibits an intermediate burst.

Figure 5:
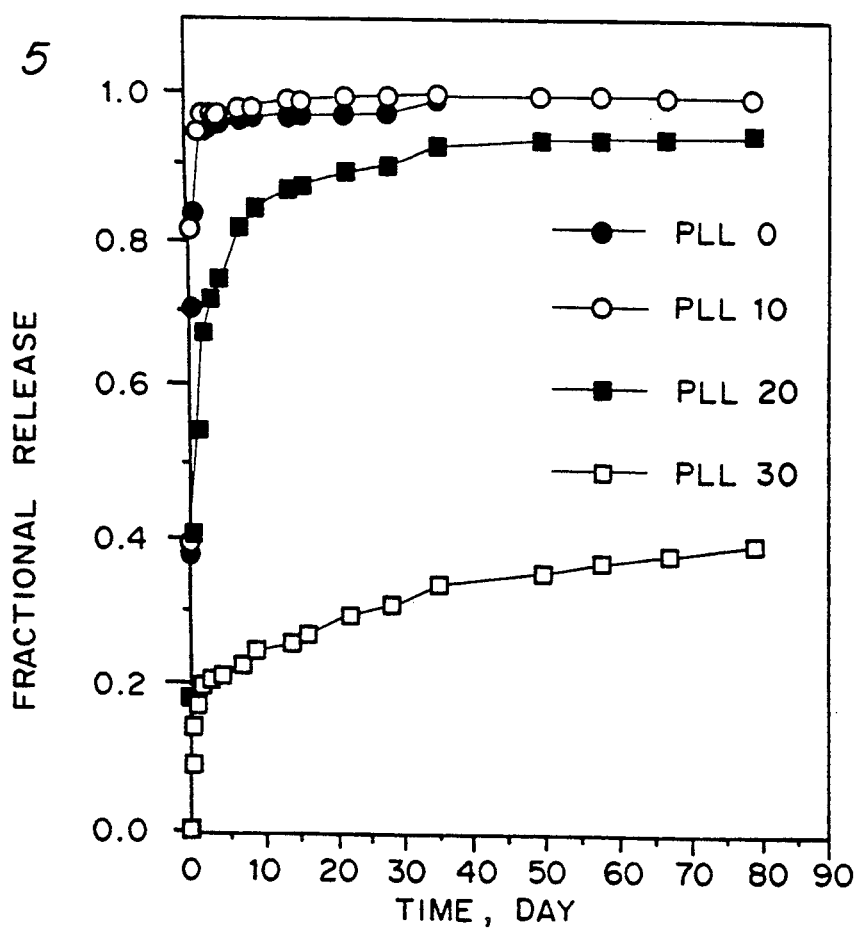
FIG. 5 is a graph of the fractional release over time (days), demonstrating the effect of L-101 blending on BSA release. PLL X indicates X% weight fraction of L-101.

The slow release of BSA may be explained by the morphological changes that occur in the interconnecting porous channels of PLA blended with L-101 upon hydration. When blend films are incubated in aqueous solution, water penetrates into the matrices to first hydrate the amorphous region of the PLA/Pluronic TM blend. As a result, the PLA/L-101 blend acquires a liquid crystalline phase which fills the pores. This phase holds the BSA molecules within the pores and prevents their fast release. This is supported by the finding that the release rates of BSA can be controlled by the amount of L-101 that is incorporated into the blends, as shown in FIG. 5. Thirty percent (w/w) L-101 in the blend resulted in a system that controlled the release of BSA for more than 80 days while the 10% in the blend more than 95% of the BSA was released after 3 days of incubation.

There have been a few studies on the liquid crystalline phase formed by nonionic surfactant-water interaction, yet its physical nature is not well understood. It was reported by Tiemessen, et al., *J. Controlled Release* 13, 73-81 (1990), that a mixture of water and nonionic surfactant, Brij 96 (polyoxyethylene(10) oleylether) possibly exhibits a variety of liquid crystalline structures such as lamellar, viscous isotropic, and hexagonal gel, depending on the mixing ratio. The different liquid crystalline phases demonstrated different diffusion coefficients for a particular drug due to changes in the morphology of the aqueous porosities and tortuosities. Protein release from the liquid crystalline phase should occur via arrays of hydrophilic and aqueous pores created by the self-assembled hydrophobic domains. It is, therefore, likely that the macromolecular protein has a low effective diffusion coefficient in such a creamy gel structure, since the aqueous porous channels have a relatively small volume compared to the hydrophobically organized domains.

In summary, it has been shown that PLA can be physically blended with nonionic polymeric surfactants, Pluronics TM, to form a matrix where the surfactant may be entangled in the amorphous region of PLA. Upon hydration, the blends acquire an additional liquid crystalline phase that is now imbedded between the PLA crystalline phase, producing an overall intact surface morphology. This results in drug release profiles with a minimum initial protein burst and a longer term release.

Modifications and variations of the polymeric compositions, and methods of manufacture and use thereof, will be obvious to those skilled in the art from the foregoing detailed description. Such modifications and variations are intended to come within the scope of the following claims.

We claim:

1. A method for controlled release comprising
   blending a biocompatible, non-toxic polymer degrading by hydrolysis selected from the group consisting of poly(lactic acid), poly(glycolic acid), polyorthoesters, polyanhydrides, and poly(amino acids) and block copolymers of polyethyleneoxide and polypropyleneoxide in a ratio between 10:90 and 90:10 of polymer to block copolymer,
   mixing into the blend a compound to be released, and
   delivering the blend containing the compound to the site where release is to be achieved.

2. The method of claim 1 wherein the compound is selected from the group consisting of inorganic compounds, proteins, carbohydrates, and non-protein organic molecules.

3. The method of claim 1 wherein the blend is formed into microspheres for controlled release of the incorporated compound.

* * * * *